(12) United States Patent
Bell et al.

(10) Patent No.: US 10,444,044 B2
(45) Date of Patent: Oct. 15, 2019

(54) FLOW MEASUREMENT SYSTEMS AND METHODS

(71) Applicants: Joel David Bell, Katy, TX (US); Zaki Din Husain, Katy, TX (US)

(72) Inventors: Joel David Bell, Katy, TX (US); Zaki Din Husain, Katy, TX (US)

(*) Notice: Subject to any disclaimer, the term of this patent is extended or adjusted under 35 U.S.C. 154(b) by 0 days.

(21) Appl. No.: 16/057,907

(22) Filed: Aug. 8, 2018

(65) Prior Publication Data

US 2019/0137308 A1 May 9, 2019

Related U.S. Application Data

(63) Continuation-in-part of application No. 15/420,157, filed on Jan. 31, 2017, now Pat. No. 10,054,472.

(51) Int. Cl.
*G01F 1/42* (2006.01)
*G01F 1/36* (2006.01)
*G01N 9/00* (2006.01)

(52) U.S. Cl.
CPC .............. *G01F 1/42* (2013.01); *G01F 1/363* (2013.01); *G01N 9/00* (2013.01)

(58) Field of Classification Search
CPC .......... G01F 1/44; G01F 232/00; G01F 25/00; G01F 1/42; G01F 1/36
See application file for complete search history.

(56) References Cited

U.S. PATENT DOCUMENTS

| 7,357,040 B2* | 4/2008 | Bell | G01F 1/40 73/861.52 |
| 8,136,414 B2* | 3/2012 | Steven | G01F 1/3209 73/861.63 |
| 2011/0214757 A1* | 9/2011 | Igarashi | G01F 1/363 137/511 |
| 2012/0180547 A1* | 7/2012 | Lawrence | G01F 25/0007 73/1.35 |
| 2013/0312421 A1* | 11/2013 | Palczewski | F02C 7/232 60/772 |
| 2018/0253111 A1* | 9/2018 | Goto | G01F 25/0007 |
| 2018/0345308 A1* | 12/2018 | Chandran | G01F 23/0069 |

* cited by examiner

*Primary Examiner* — Jewel V Dowtin
(74) *Attorney, Agent, or Firm* — Shawn Hunter (57) ABSTRACT

A fluid flow measurement system for measuring the flow rate, density and/or other flow parameters of fluid flow through a flowbore. Additionally, the devices and methods advantageously provide for sampling of the fluid flow from different locations within the flow stream (i.e., center, proximate flowbore wall).

12 Claims, 6 Drawing Sheets

FLOW MEASUREMENT SYSTEMS AND METHODS

BACKGROUND OF THE INVENTION

1. Field of the Invention

The invention relates generally to devices and methods for measuring the volume, density and or other parameters of fluid flowing through a flowbore.

2. Description of the Related Art

Flow meters are used to measure the volume of fluid flow through a flowbore. Flow meters are widely used in many industries for many types of fluids. A torus wedge flow meter is described in U.S. Pat. No. 7,357,040 entitled "Torus Wedge Flow Meter" issued Apr. 15, 2008. This patent is commonly owned with the present application and is herein incorporated by reference in its entirety.

Fluid pressure is normally measured upstream of a flow restriction and downstream of the flow restriction. The measured pressure differential will allow calculation of fluid flow rate. Conventional wisdom is to place any protrusion for sampling or density measurement devices a substantial distance downstream from flow restrictions, such as orifice plates, wherein downstream fluid pressure is measured. It is typically suggested to space such downstream devices a minimum distance equal to five times the diameter of the flowbore or pipe interior diameter. This requirement is generally imposed on differential pressure-type flow meters to eliminate any possible influence on the pressure monitored at the downstream pressure tap due to turbulent disturbances and flow restriction resulting from the inserted probe for collecting samples or for monitoring the density or viscosity of the flowing fluid. The desire for substantial distancing of measurement devices leads to widely separated measurement devices, which the inventor believes is undesirable.

It is also noted that current flow diagnostic techniques can generally measure particular flow characteristics, such as a change in pressure or in flow rate. However, these flow diagnostic tools are not particularly useful for determining when such a change has occurred. Currently, such flow characteristic measurements are made after the fact (i.e., once a problem is suspected) leaving an operator to speculate as to what affected the fluid flow to cause the measured change.

SUMMARY OF THE INVENTION

The invention provides devices and methods for measuring the flow rate, density and/or other flow parameters of fluid flowing through a flowbore. Additionally, the devices and methods of the current invention advantageously provide for sampling of the fluid flow from different locations within the flow stream (i.e., center, proximate flowbore wall).

An exemplary flow measurement system is described which can be incorporated into a pipeline or other flow line through which fluid is flowed. The flow measurement system is particularly well suited to measurement of flow parameters for multiple phase fluids which include less viscous components (i.e., water) and more viscous components (i.e., hydrocarbons). In particular embodiments, the flow measurement system is capable of measuring flow rate, fluid pressure and fluid density as well as for taking selective samples of fluid flowing within the flowbore.

A described flow measurement system has placement of downstream sampling devices relatively close to the flow rate measurement components of the system. In preferred embodiments, sampling devices are axially spaced apart from the flow rate measurement components within a length that is significantly shorter, and preferably equal to or less than five times the diameter of the flowbore. This also allows for a compact design for lower maintenance costs and ownership costs. The inventors also believe that measuring fluid properties (e.g., density and/or viscosity) of the flow by a probe placed within the highly mixed flow downstream of and proximate to the flow restriction will ensure that the fluid is well mixed and sampled or measured fluid at this location will be better representative of the actual water content of the fluid.

In a described embodiment, the flow measurement system includes staged measurement rings. A first measurement ring is provided in which fluid pressure is detected. The second measurement ring is downstream of the first measurement ring. The second measurement ring includes a flow restriction and, as well, allows fluid pressure detection at the point of flow restriction. A third measurement ring is located downstream of the first and second measurement rings. The third measurement ring allows for fluid pressure detection. Preferably also, the third measurement ring allows for fluid sampling. In preferred embodiments, one or more fluid samplers and/or densitometers are located downstream of the staged measurement rings.

Pressure detection taps on each of the measurement rings are interconnected with a differential pressure detector. Valves, such as solenoid valves, are used to control fluid communication between the pressure detection taps and the differential pressure detector.

The valves and any downstream samplers and densitometers are preferably operably interconnected with a programmable logic controller which is provided with suitable programming to operate the valves and samplers in accordance with a preprogrammed scheme. Additionally, the controller is preferably programmed to receive information from various sensors within the system relating to fluid flow characteristics. Preferably also, the controller is programmed to conduct calculations to determine pressure differentials based upon measured pressures. Preferably also, the controller includes a timer.

Comparison of detected differential pressures will yield a ratio of differential pressures. Changes in this ratio may indicate a change in flow characteristics for fluid flowing through the flowbore. The detection and comparison steps can be used as a diagnostic tool since changes in the ratio can be correlated to one or more particular times leading to identification of the cause of the change.

In accordance with a preferred embodiment of the invention, the flow characteristic detection is bi-directional such that the direction of flow within the flowbore can be reversed and reverse differential pressures obtained by the controller. When fluid flow is reversed, the formerly downstream pressure detection tap becomes the new upstream pressure detection tap while the former upstream pressure detection tap becomes the new downstream pressure detection tap.

According to a further aspect of the invention, a fluid flow meter is described which could be used as the second measurement ring for the flow measurement system. An exemplary fluid flow meter includes a flow meter body which defines a central flow passage along its axial length. The central flow passage has a flow restriction opening which provides a point of maximum reduced flow area for the central flow passage. A pressure measurement port is formed within the flow meter body and is in fluid communication with the flow restriction opening to allow fluid pressure at the flow restriction opening to be measured. Upstream and downstream angled faces extend away from the flow restriction opening within the central flow passage. A semi-circular or arcuate groove is formed within the upper portion of the flow restriction opening. The groove is in fluid communication with the pressure measurement port and serves to equalize the fluid pressure surrounding the pressure measurement port, thereby leading to more accurate pressure measurements.

BRIEF DESCRIPTION OF THE DRAWINGS

For a thorough understanding of the present invention, reference is made to the following detailed description of the preferred embodiments, taken in conjunction with the accompanying drawings, wherein like reference numerals designate like or similar elements throughout the several figures of the drawings and wherein.

DETAILED DESCRIPTION OF THE PREFERRED EMBODIMENTS

Figure 1:
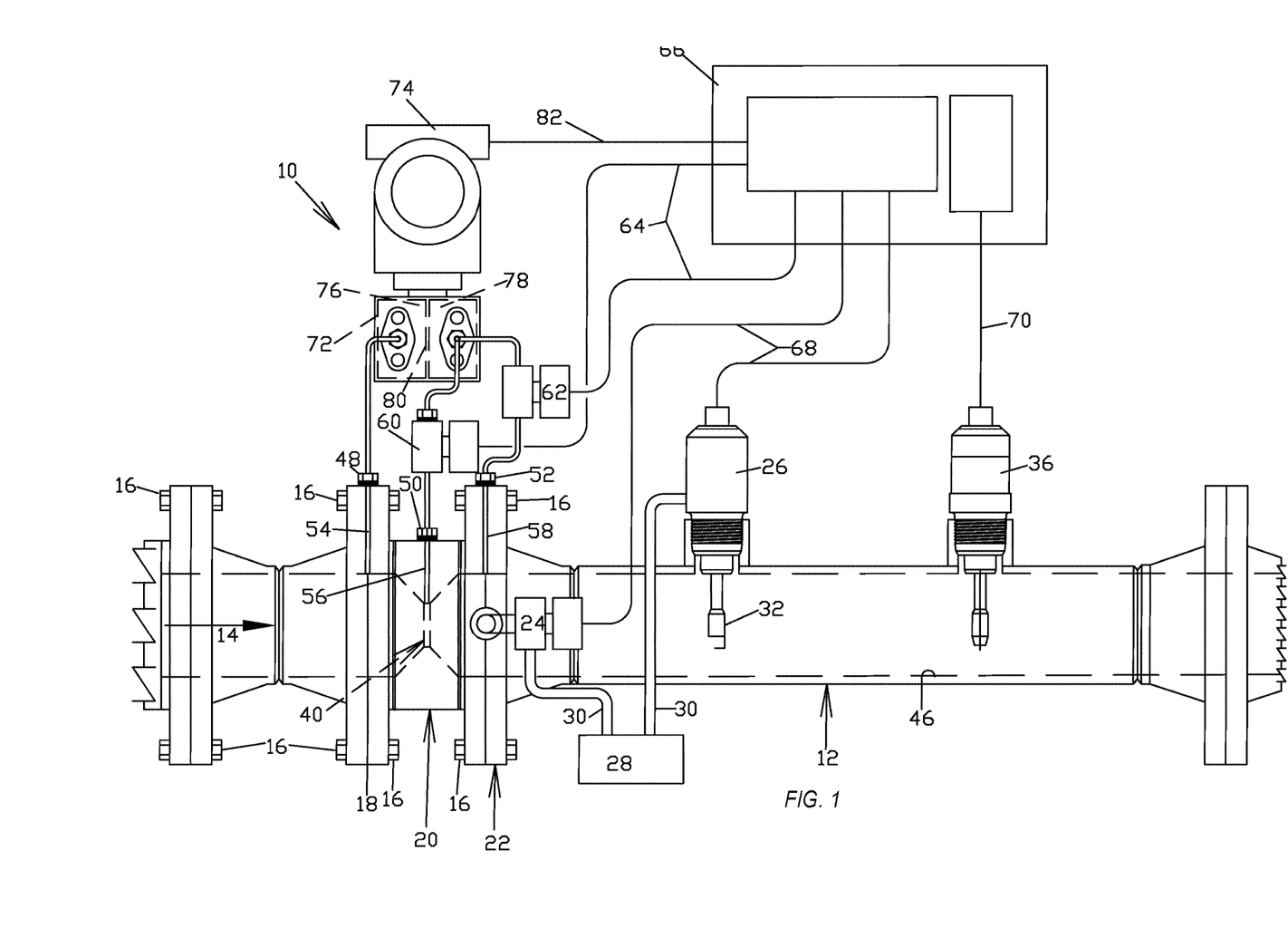
FIG. 1 is a schematic view of an exemplary flow measurement system in accordance with the present invention.

FIG. 1 depicts an exemplary flow measurement system 10 which has been constructed in accordance with the present invention. The flow measurement system 10 is incorporated into pipeline or other flowbore 12. Fluid passes through the flowbore 12 in the direction indicated by arrow 14. The fluid can be a single-phase or a multi-phase fluid. The pipeline making up flowbore 12 may have any desired construction, including flanged piping sections which are interconnected with nuts and bolts 16 in an end-to-end fashion, as is well known in the art.

In described embodiments, the flow measurement system 10 provides the ability to measure volume, density and viscosity for fluid passing through the flowbore 12. The flow measurement system 10 can be advantageously installed as a compact system within an existing pipeline.

Figure 2:
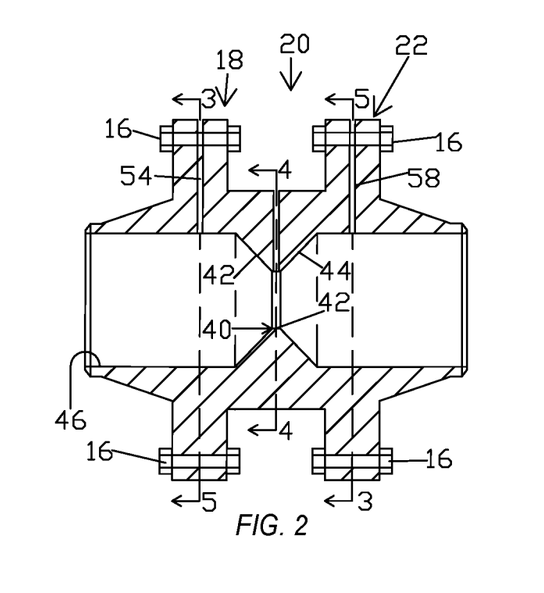
FIG. 2 is an enlarged, cross-sectional view of a portion of the flow measurement system shown in FIG. 1.

As depicted in FIGS. 1 and 2, the flow measurement system 10 defines a set of three successive flow measurement rings, indicated at 18, 20, 22 and which are located within the flowbore 12. In preferred embodiments, a first fluid sampler 24 is operably interconnected with the third flow measurement ring 22. A second fluid sampler 26 preferably is incorporated into the flowbore 12 downstream of the third flow measurement ring 22.

A sample storage container 28 is operably associated with both the first and second fluid samplers 24 and 26 via tubing 30 so that fluid samples obtained by the first and second fluid samplers 24, 26 are deposited into the sample storage container 28. It is noted that the second fluid sampler 26 includes a sample collection probe 32 which extends into the flowbore 12 so that fluid is collected into the probe 32 at or near the approximate center of the flowbore 12. The first fluid sampler 24 preferably obtains fluid samples from the outer radial periphery of the flowbore 12 via passageway 34 (see FIG. 5).

A densitometer 36 is also preferably incorporated into the flowbore 12 and is operable to measure fluid temperature, density and/or viscosity for fluid passing through the flowbore 12. A suitable densitometer for use as densitometer 36 is a Rheonics SRD in-line process density and viscosity measurement device.

Figure 3:
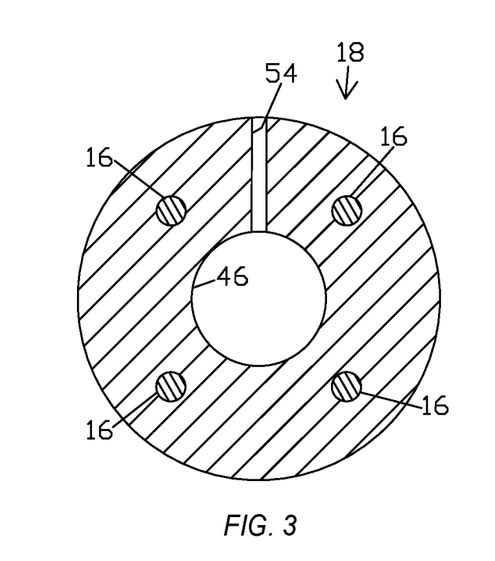
FIG. 3 is a cross-sectional view taken along lines 3-3 in FIG. 2.
Figure 4:
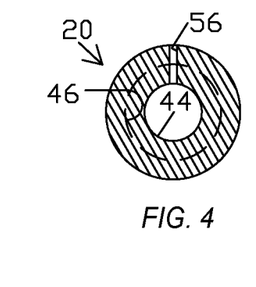
FIG. 4 is a cross-sectional view taken along lines 4-4 in FIG. 2.
Figure 5:
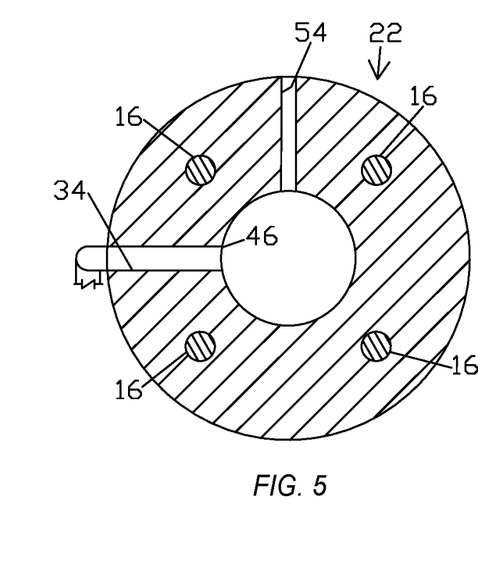
FIG. 5 is a cross-sectional view taken along lines 5-5 in FIG. 2.

The construction and operation of the flow measurement rings 18, 20 and 22 is better appreciated with further reference to FIGS. 3-5. A fluid flow restriction, generally indicated at 40, is formed within the second measurement ring 20. The fluid flow restriction 40 is a reduced diameter opening which is defined by a generally circular sill 42. Angled surfaces 42 and 44 extend inwardly from the interior diameter 46 of the flowbore 12 to the sill 42.

A number of pressure taps are incorporated into the first, second and third measurement rings 18, 20 and 22, thereby permitting fluid pressure to be detected upstream, at and downstream of the fluid flow restriction 40. Pressure taps 48, 50, 52 are operably associated with lateral fluid passageways 54, 56 and 58, respectively. The lateral fluid passageways are defined within the first, second and third measurement rings 18, 20, 22, respectively.

Solenoid-controlled valves 60, 62 are operably associated with the pressure taps 50 and 52, respectively. Control lines 64 extend between each of the valve 60, 62 and a programmable logic controller 66. Additional control lines 68 extend between the controller 66 and the first and second samplers 24, 26. Control line 70 extends between the controller 66 and the densitometer 36.

The exemplary flow measurement system 10 includes a flow manifold 72 and operably associated differential pressure measurement device 74. It is noted that the flow manifold 72 receives fluid into either a first chamber 76 or a second chamber 78 which are separated by a flexible membrane 80. Deflection of the membrane is measured by the differential pressure measurement device 74 and is indicative of the differential pressure between the first and second chambers 76, 78. A suitable differential pressure measurement device for use as the device 74 is a remote seal pressure transmitter which is available commercially from a number of manufacturers. The flow manifold 72 is plumbed such that fluid from the first pressure tap 48 and first measurement ring 18 is directed into the first chamber 76. Fluid from either the second pressure tap 50 (second measurement ring 20) or the third pressure tap 52 (third measurement ring 22) is directed into the second chamber 78. Data communication line 82 extends between the differential pressure measurement device 74 and the controller 66.

The programmable logic controller 66 is provided with suitable programming to operate the solenoid valves 60, 62 and samplers 24, 26 in accordance with a preprogrammed scheme. Additionally, the controller 66 is preferably programmed to receive differential pressure readings from the differential pressure measurement device 74 as well as density, viscosity and/or temperature readings from the densitometer 36. Preferably also, the controller 66 includes a clock or timer so that control functions and detection of particular flow parameters can be performed at predetermined intervals. The controller 66 may be provided with a display and/or memory storage, as is known in the art, for recording of detected flow parameters over time.

In operation, fluid is flowed through the flowbore 12 in the direction indicated by arrow 14. Fluid enters the flow measurement system 10 and passes through the first, second and third measurement rings 18, 20, 22. As this occurs fluid pressure at the first pressure tap 48 is communicated to the first chamber 76 of the flow manifold 72 (for a pressure of P1 at an upstream location). The controller 66 alternately opens and closes the solenoid valves 60 and 62 such that the second chamber 78 communicates with fluid pressure from either the second pressure tap 50 or the downstream pressure at the third pressure tap 52. It should be understood that fluid pressure at the second pressure tap 50 is indicative of fluid pressure at the flow restriction 40 (pressure of P2) while fluid pressure at the third pressure tap 52 is indicative of fluid pressure downstream of the flow restriction 40 (pressure of P3 at a downstream location). Thus, when the second chamber 78 is exposed to fluid pressure from the second pressure tap 50, the differential pressure detected will be (P1–P2). When the second chamber 78 is exposed to fluid pressure from the third pressure tap 52, the differential pressure will be (P1–P3).

Preferably, the controller 66 calculates a ratio of the detected differential pressures (P1–P3/P1–P2). The ratio can be recorded over time and used as a diagnostic tool for fluid flow through the flowbore 12. A change in the ratio would indicate a change in the characteristics of the fluid flowing through the flowbore 12, such as flow rate or pressure.

It is noted that the flow measurement system 10 preferably has a compact design which permits it to be incorporated into a flowbore 12 without needing to widely separate the components out physically. In particular, the second sampler 26 and densitometer 36 can be, and preferably are, located axially downstream of the third measurement ring 22 within five interior diameters 46 of the flowbore 12. Additionally, it is noted that the second sampler 26 and densitometer 36 may be placed adjacent to one another, including in actual contact with one another, without affecting their essential operation.

It is also noted that the flow measurement system 10 is particularly well adapted for instances wherein there is bidirectional fluid flow which must be measured. For instance, in cavern storage of hydrocarbon fluid, the fluid to be stored is flowed through flowbore 12 in a first direction, indicated by arrow 14 in FIG. 1, into the cavern. When it is desired to remove fluid from the cavern, fluid can be pumped through the same flowbore 12 in the opposite direction. When this is done, the third measurement ring 22 functions to detect an upstream pressure (P1), and the first measurement ring 18 functions to detect a downstream pressure (P3). In other words, the upstream and downstream locations are now swapped so that the third pressure tap 52 detects an upstream pressure and the first pressure tap 48 detects a downstream pressure. Those of skill in the art will recognize that some minor re-plumbing of the system 10 would be needed in order to successfully allow proper measurement of flow in a reverse direction. For example, the second sampler 26 and densitometer 36 would preferably be relocated to the opposite side of the first measurement ring 18 so that they will be downstream of flow through the flow restriction 40. In accordance with preferred embodiments, the controller 66 is programmed to determine a new differential pressure ratio when the flow direction within the flowbore is reversed. In particular, the new upstream pressure ($P1^N$) is detected by the third measurement ring 22 and third pressure tap 52. The new downstream pressure ($P3^N$) is detected by the first measurement ring 18 and first pressure tap 48. The controller 66 then determines the new differential pressure ratio ($P1^N$–$P3^N$/$P1^N$–P2).

The flow measurement system 10 of the present invention also provides for representative sampling of the fluid flow within the flowbore 12. During operation, the first sampler 24 obtains a fluid sample from a peripheral edge of the interior diameter 46 of the flowbore 12. This sample is also obtained directly after the fluid flow passes through the flow restriction 40 and is thereby subject to some turbulence which would tend to mix the fluid components. The second sampler 26 obtains a fluid sample from the approximate axial center of the flow via probe 32. Samples from both the first and second samplers 24, 26 are then comingled within the sample storage container 28. These techniques ensure that the sample storage container 28 will contain representative samples of the fluid flowing through the flowbore 12. The inventors consider this feature to be advantageous particularly where multi-phase fluids are involved. Multi-phase fluids, composed, for example, of oil, water and gas components, have significantly lower surface tension than water. Components will readily atomize and tend to remain suspended as a homogeneous mixture with flowing gas at relatively low flow velocity, while water with much higher surface tension tends to adhere to flowbore surfaces over a relatively wide range of flow velocities. The tapering provided by the angled surfaces 42 or 44 of the second measurement ring 20 tends to effectively scoop or lift fluid from the interior surfaces of the flowbore 12 and force it through the flow restriction 40. At relatively low flow rates, the flow restriction 40 mixes water droplets as suspended liquid within the gas an atomized hydrocarbon mixture. Further downstream from the flow restriction, water particles would gradually drop out of the mixture and again begin to adhere to the surfaces of the flowbore 12. Therefore, locating the second sampler 26 proximate the flow restriction 40 will provide a more representative sample of the fluid flowing through the flowbore 20 than would a sampler located further downstream (i.e., at least 5 flowbore diameters) from the flow restriction 40 as water droplets which would otherwise drop out of the mixture will be captured.

Figure 6:
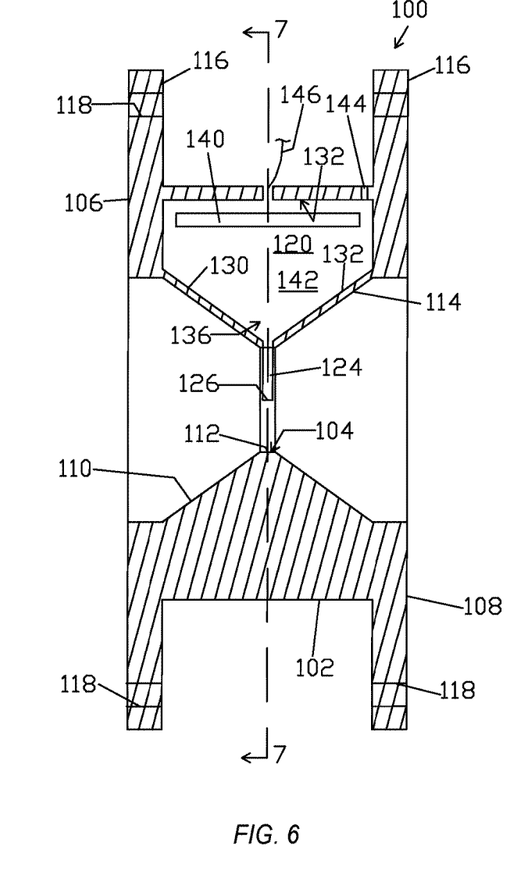
FIG. 6 is a side, cross-sectional view of an exemplary alternative flow meter ring constructed in accordance with the present invention.
Figure 7:
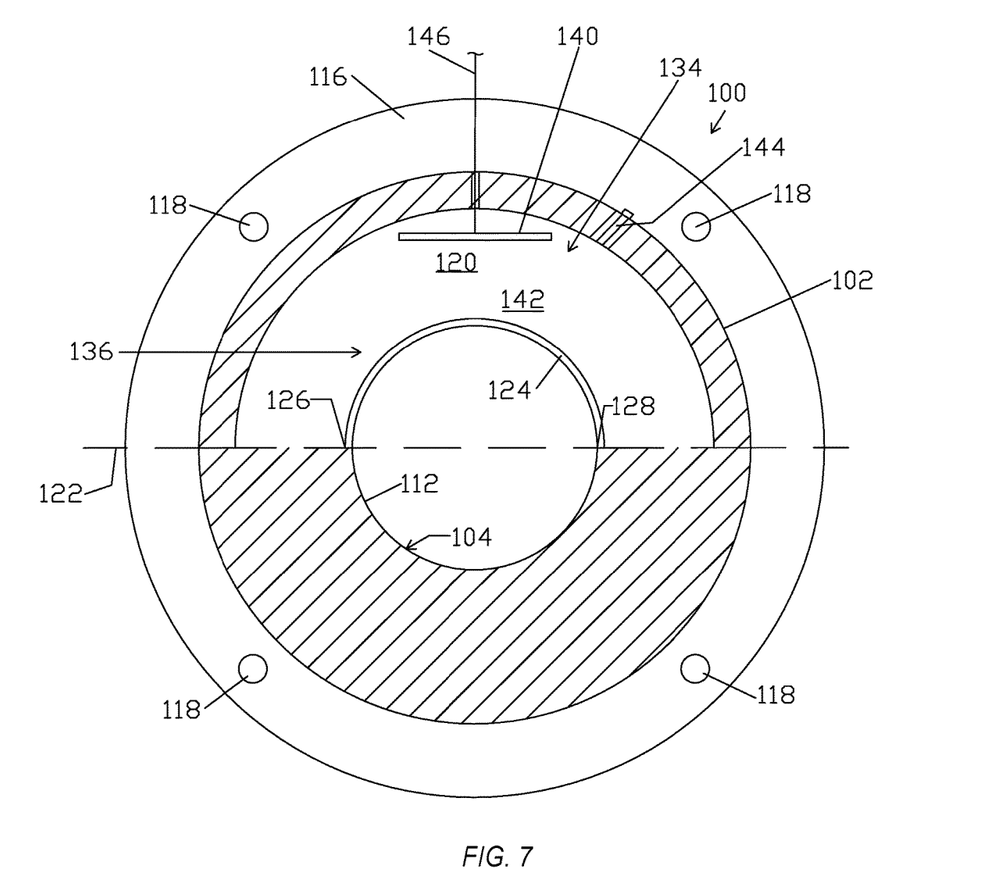
FIG. 7 is a cross-sectional view of the flow meter ring of FIG. 6, taken along lines 7-7 in FIG. 6.

The second flow measurement ring 20 of the flow measurement system 10 includes a flow restriction 40 and fluid pressure passage 56. The second flow measurement ring 20 may be constructed and operate in the manner as the inventive flow meter described in U.S. Pat. No. 7,357,040 ("Torus Wedge Flow Meter"). The second flow meter ring 20 may also be constructed in the manner shown in FIGS. 6-7. FIGS. 6-7 depict a flow meter ring 100 which is operable to detect the rate of fluid flow through a flowbore. The ring 100 includes a ring body 102 which defines a central opening 104. The central opening 104 will serve as the flow restriction 40 described above. The ring body 102 presents a first axial side 106 and a second axial side 108. A to first angled surface 110 extends from the first axial side 106 to a flat sill 112 which defines the central opening 104. A second angled surface 114 extends from the second axial side 108 to the sill 112.

Preferably, the ring body 102 includes radially outwardly projecting flanges 116. Bolt openings 118 are disposed through the flanges 116 so that the flow meter ring 100 can be secured to adjacent components.

A chamber 120 is formed within what is considered the uppermost portion of the ring body 102. The portion above the line 122 in FIG. 7 is considered to be the "upper" portion of the ring 100. A slit 124 is formed within the upper portion of the sill 112 and allows fluid communication between the central opening 104 and the chamber 120. In the depicted embodiment, the slit 124 extends from a first end point 126 to a second end point 128 so as to circumscribe an approximate semi-circle within the ring body 102. In alternative embodiments, the slit 124 may describe an arc which is less than a complete semi-circle or somewhat more than a semi-circle. The slit 124 functions to equalize or average out the fluid pressure which is transmitted into the chamber 120 from the central opening 104 during fluid flow through the central opening 104. The inventors believe that this provides for more accurate and reliable pressure readings. As shown in FIG. 6, the chamber 120 has side surfaces 130, 132 which diverge such that the upper, radially outermost portion 134 of the chamber 120 is larger than the lower, radially innermost portion 136 of the chamber 120 which is proximate the slit 124. As a non-limiting example, the surface area defining the upper, radially outermost portion 134 may be about 4.5 square inches while the surface area defining the lower innermost portion 136 may be about 0.5". This feature permits the chamber 120 to be self-cleaning as any fluid entering the chamber 120 can drain out through the slit 124. In addition, the slit 124 is unlikely to clog and prevent fluid pressure transmission into the chamber 120 due to arcuate, generally semi-circular configuration.

In accordance with particular embodiments, a fluid property detector in the form of a pressure detector 140 is disposed within the chamber 120. The pressure detector 140 may be a pressure transducer or other device(s) capable of detecting pressure within the surrounding chamber 120 and/or useful to determine or calculate flow rate. In other embodiments, the fluid property detector 140 may detect temperature or other fluid properties. Preferably, the pressure detector 140 is disposed within an uppermost section of the chamber 120 such that a buffer area 142 is interposed between the pressure detector 140 and the slit 124. This placement permits the pressure detector 140 to sense static pressure rather than changing pressures associated with the fluid flow through the central opening 104.

In preferred embodiments, a gas bleed valve 144 is disposed through the ring body to permit pressure to be released from within the chamber 120. During operation, the gas bleed valve 144 would be closed so that pressure within the chamber 120 is contained. Prior to operation, the gas bleed valve 144 may be opened to evacuate the chamber 120. Preferably also, a cable 146 passes through the ring body 102 in order to interconnect the pressure detector 140 with the controller 66.

In operation, fluid flowing through the flowbore 12 will encounter the flow meter ring 100 be forced through the flow restriction 104 of the ring body 102. Fluid communication via the slit 124 causes the chamber 120 to be at the same pressure as the fluid flowing through the flow restriction 104 while buffering the detector 140 from experiencing fluctuations resulting from the turbulence of flow through the flow restriction 104. During operation, the chamber 120 is largely self-draining of any fluid which might enter the chamber 120 through the slit 124 back into the flow restriction 104. The slit 124 is also largely clog resistant due to the length of the slit 124.

What is claimed is:

1. A flow measurement system for measuring one or more fluid flow characteristics of a fluid flowing through a flowbore from an upstream direction toward a downstream direction, the system comprising:
   a flow restriction within the flowbore;
   a first pressure detection tap located in the upstream direction from the flow restriction, the first pressure detection tap detecting fluid pressure at an upstream location which is upstream of the flow restriction;
   a second pressure detection tap located at the flow restriction to detect fluid pressure within the flowbore at the flow restriction;
   a third pressure detection tap located in the downstream direction from the flow restriction, the third pressure detection tap detecting fluid pressure within the flowbore at a downstream location which is downstream of the flow restriction;
   a differential pressure measurement device which measures a first differential pressure, the first differential pressure being the difference between a pressure at the first pressure detection tap versus a pressure at the second pressure detection tap; and
   the differential pressure measurement device further measures a second differential pressure, the second differential pressure being a pressure at the first pressure detection tap versus a pressure at the third pressure detection tap.

2. The flow measurement system of claim 1 further comprising:
   a programmable logic controller which is operably interconnected with the differential pressure measurement device; and wherein
   the programmable logic controller obtains the first and second differential pressures; and determines a ratio of the first differential pressure to the second differential pressure.

3. The flow measurement system of claim 2 further comprising:
   a flow manifold operably associated with the differential pressure measurement device; and
   at least one valve to control fluid pressure communication to the flow manifold as between either the second pressure detection tap or the third pressure detection tap.

4. The flow measurement system of claim 1 wherein the flowbore has a central axis and a peripheral edge and wherein the flow measurement system further comprises:
   a first fluid sampler which obtains a first fluid sample from the fluid flowing through the flowbore proximate the peripheral edge;
   a second fluid sampler which obtains a second fluid sample from the fluid flowing through the flowbore proximate the central axis; and
   a sample storage container into which the first and second fluid samples are deposited.

5. The flow measurement system of claim 4 wherein the flowbore has a diameter and wherein:
   the second fluid sampler is spaced apart from the first fluid sampler along the flowbore by a distance that is less than or equal to five times the diameter of the flowbore.

6. The flow measurement system of claim 2 wherein fluid flow within the flowbore is further reversed such that:
   the third pressure detection tap detects fluid pressure at a new upstream location which is now upstream of the flow restriction;
   the first pressure detection tap detects fluid pressure at a new downstream location which is now downstream of the flow restriction;
   the programmable logic controller obtains a new first differential pressure measurement which is the difference of a pressure at the new upstream location versus a pressure at the second pressure detection tap;
   the programmable logic controller obtains a new second differential pressure measurement which is the difference of a pressure at the new upstream location versus a pressure at the new downstream location; and the programmable logic controller determines a ratio of the new first differential pressure to the new second differential pressure.

7. The flow measurement system of claim 1 further comprising a flow meter ring which includes:
 a ring body defining a central opening which is defined by a sill;
 a chamber formed within the ring body radially outside of the central opening;
 a slit formed within the sill of the ring body to provide fluid communication between the central opening and the chamber; and
 a fluid property detector disposed within the chamber.

8. The flow measurement system of claim 7 wherein the fluid property detector comprises a fluid pressure detector.

9. The flow measurement system of claim 7 wherein the slit extends along the sill from a first end point to a second end point to form an approximate semi-circle.

10. A method of measuring one or more fluid flow characteristics of a fluid flowing through a flowbore from an upstream direction toward a downstream direction, the method comprising the steps of:
 flowing the fluid through a flow restriction in the flowbore, the flowbore having a central axis and a peripheral edge;
 obtaining a first fluid sample from the fluid flowing through the flowbore proximate the peripheral edge;
 obtaining a second fluid sample from the fluid flowing through the flowbore proximate the central axis;
 depositing the first and second fluid samples into a sample storage container;
 detecting upstream fluid pressure at a first location which is upstream of the flow restriction;
 detecting fluid pressure at a second location which is at the flow restriction;
 detecting downstream fluid pressure at a third location which is downstream of the flow restriction.

11. The method of claim 10 further comprising the steps of:
 determining a first differential pressure, the first differential pressure being the difference between the upstream fluid pressure at the first location versus the fluid pressure at the second location;
 determining a second differential pressure, the second differential pressure being the difference between the upstream fluid pressure at the first location versus the downstream fluid pressure at the third location; and
 determining a ratio of the first pressure differential to the second pressure differential.

12. The method of claim 10 further comprising the steps of:
 reversing fluid flow through the flowbore;
 thereafter, determining a new upstream fluid pressure at the third location; and determining a new downstream fluid pressure at first location.

* * * * *